(12) United States Patent
Schmieding et al.

(10) Patent No.: US 7,077,863 B2
(45) Date of Patent: *Jul. 18, 2006

(54) TRANSVERSE FIXATION TECHNIQUE FOR ACL RECONSTRUCTION USING BONE-TENDON-BONE GRAFT WITH LOOP AT END

(75) Inventors: Reinhold Schmieding, Naples, FL (US); Jeffery M. Whelan, Sugar Land, TX (US)

(73) Assignee: Arthrex, Inc., Naples, FL (US)

( * ) Notice: Subject to any disclaimer, the term of this patent is extended or adjusted under 35 U.S.C. 154(b) by 571 days.

This patent is subject to a terminal disclaimer.

(21) Appl. No.: 10/370,564

(22) Filed: Feb. 24, 2003

(65) Prior Publication Data

US 2003/0176919 A1 Sep. 18, 2003

Related U.S. Application Data

(63) Continuation-in-part of application No. 10/280,028, filed on Oct. 25, 2002, which is a continuation-in-part of application No. 10/121,610, filed on Apr. 15, 2002, now Pat. No. 6,537,319, which is a continuation of application No. 09/663,798, filed on Sep. 18, 2000, now Pat. No. 6,371,124, which is a continuation of application No. 09/346,709, filed on Jul. 2, 1999, now Pat. No. 6,132,433, which is a continuation of application No. 09/015,618, filed on Jan. 29, 1998, now Pat. No. 5,918,604.

(60) Provisional application No. 60/037,610, filed on Feb. 12, 1997, provisional application No. 60/330,575, filed on Oct. 25, 2001.

(51) Int. Cl.
*A61B 2/08* (2006.01)
*A61B 17/56* (2006.01)

(52) U.S. Cl. .................. 623/13.14; 606/72; 606/99; 128/898

(58) Field of Classification Search ............. None
See application file for complete search history.

(56) References Cited

U.S. PATENT DOCUMENTS

| 4,985,032 A | 1/1991 | Goble |
| 5,098,435 A | 3/1992 | Stednitz et al. |
| 5,266,075 A | 11/1993 | Clark et al. |

(Continued)

FOREIGN PATENT DOCUMENTS

FR 268 4543 6/1993

OTHER PUBLICATIONS

C. Harner et al., "Anterior Cruciate Ligament Reconstruction: Endoscopic Versus Two-Incision Technique", Arthroscopy: vol. 10, No. 5, pp. 501-512 (1994).

(Continued)

*Primary Examiner*—Julian W. Woo
*Assistant Examiner*—Sarah Webb
(74) *Attorney, Agent, or Firm*—Dickstein Shapiro Morin & Oshinsky LLP

(57) ABSTRACT

A surgical method for transosseous fixation of a bone-tendon-bone (BTB) graft into a joint is disclosed. A longitudinal tunnel formed in a bone is intersected by a transverse pin. A flexible strand is drawn with the pin through the bone. A portion of the strand is diverted so as to protrude out of the entrance to the longitudinal tunnel. The strand portion is attached to a loop extending from the bone block of the BTB graft, preferably by forming the loop around the strand. The strand attached to the bone block loop is retracted into the tunnel, drawing the attached BTB graft into the tunnel. The BTB graft is fixed in the tunnel using a transverse implant passed through the loop.

8 Claims, 12 Drawing Sheets

U.S. PATENT DOCUMENTS

| | | | |
|---|---|---|---|
| 5,350,380 | A | 9/1994 | Goble et al. |
| 5,354,300 | A | 10/1994 | Goble et al. |
| 5,356,413 | A | 10/1994 | Martins et al. |
| 5,393,302 | A | 2/1995 | Clark et al. |
| 5,397,356 | A | 3/1995 | Goble et al. |
| 5,423,823 | A | 6/1995 | Schmieding |
| 5,431,651 | A | 7/1995 | Goble |
| 5,562,671 | A | 10/1996 | Goble et al. |
| 5,601,562 | A | 2/1997 | Wolf et al. |
| 5,918,604 | A | 7/1999 | Whelan |
| 6,132,433 | A | 10/2000 | Whelan |
| 6,306,138 | B1 | 10/2001 | Clark et al. |
| 6,325,804 | B1 | 12/2001 | Wenstrom et al. |
| 6,371,124 | B1 | 4/2002 | Whelan |
| 6,537,319 | B1 | 3/2003 | Whelan |
| 6,733,529 | B1 | 5/2004 | Whelan |
| 6,974,477 | B1 | 12/2005 | Whelan |
| 2002/0087160 | A1 | 7/2002 | Clark et al. |
| 2003/0176919 | A1 | 9/2003 | Schmieding |

OTHER PUBLICATIONS

B. Shaffer, et al. "Graft-Tunnel Mismatch in Endoscopic Anterior Cruciate Ligament Reconstruction: A New Technique of Intraarticular Measurement and Modified Graft Harvesting", Arthroscopy: vol. 9, No. 6, pp. 633-646 (1993).

P. Scranton, Jr., et al., "Outpatient Endoscopic Quadruple Hamstring Anterior Cruciate Ligament Reconstruction", Operative Techniques in Orthopaedics, pp. 177-180 (1996).

K. Leeds "Arthroscopic Reconstruction of the ACL With Artificial Ligament", Arthroscopy, vol. 12, No. 1, pp. 65-68 (1987).

R. Larson "Anterior Cruciate Ligament Reconstruction with Hamstring Tendons", Operative Techniques in Orthopaedics, vol. 6, No. 3, pp. 138-141 (Jul. 1996).

R. Schrer, et al., "Investment Opportunities in Orthopaedics", *Orthopaedic Industry Overview*, (Aug. 1998).

S. Howell, "ACL Reconstruction Bone Mulch Screw Washer Loc", pp. 1-14 Arthrotek, (1998).

D. McKernan, "Surgical Technique for Mitek RIGIDfix ACL Reconstruction" pp. 1-6, Mitek Products (1999).

T. Rosenberg, "Technique for ACL Reconstruction With Acufex Director Drill Guide and Endobutton CL", Smith and Nephew (1999), pp. 1-19.

F. Noyes et al., "PCL Reconstruction With the Acufex Director Drill Guide Using the Noyes All-Inside PCL Technique and a Double Bundle Quadriceps Tendon Graft".

R. Hunter, "Quadraple Loop Hamstring Graft Surgical Technique With the Phantom SofThread Interface Screw", Dpuy Orthotechnology (1998), pp. 1-8.

L. Paulos, "Endoscopic Anterior Cruciate Ligament Reconstruction", pp. 1-14, Mitek Products, Inc., (1994).

Declaration of Alan Chervitz in Support of Innovative Devices, Inc.'s Opposition to Arthrex's Motion for Partial Summary Judgement, Oct. 14, 1999, Cause No. 99-851-CIV-ORL-18C (M.D. FL).

Declaration of Wade Fallin in Support of Innovative Devices, Inc.'s Opposition to Arthrex's Motion for Partial Summary Judgment; Oct. 13, 1999, Case No. 99-851-CIV-ORL-18C (M.D. FL).

Declaration of Dennis Donnermeyer, Oct. 19, 1999, Case No. 99-851-CIV-ORL-18C (M.D. FL).

Declaration of Jeffery M. Whelan, Oct. 20, 1999, Case No. 99-851-CV-ORL-18C (M.D. FL).

DePuy Mitek Inc's Amended Answer to Arthrex's Complaint & Counterclaim, filed Oct. 14, 2004, Civil Action No. 2:04-cv-328-FTM-33DNF (M.D. FL).

Declaration of E. Marlowe Goble in Support of Innovative Devices, Inc's Opposition to Arthrex's Motion for Partial Summary Judgment (with Exhibits A, B and C), Oct. 14, 1999, Case No. 99-851-CIV-ORL-18C (M.D. FL).

Office Action, U.S. Appl. No. 09/015,618, mailed Sep. 2, 1998.

Response to Office Action, U.S. Appl. No. 09/015,618, filed Oct. 26, 1998.

U.S. Appl. No. 11/293,149, filed Dec. 5, 2005.

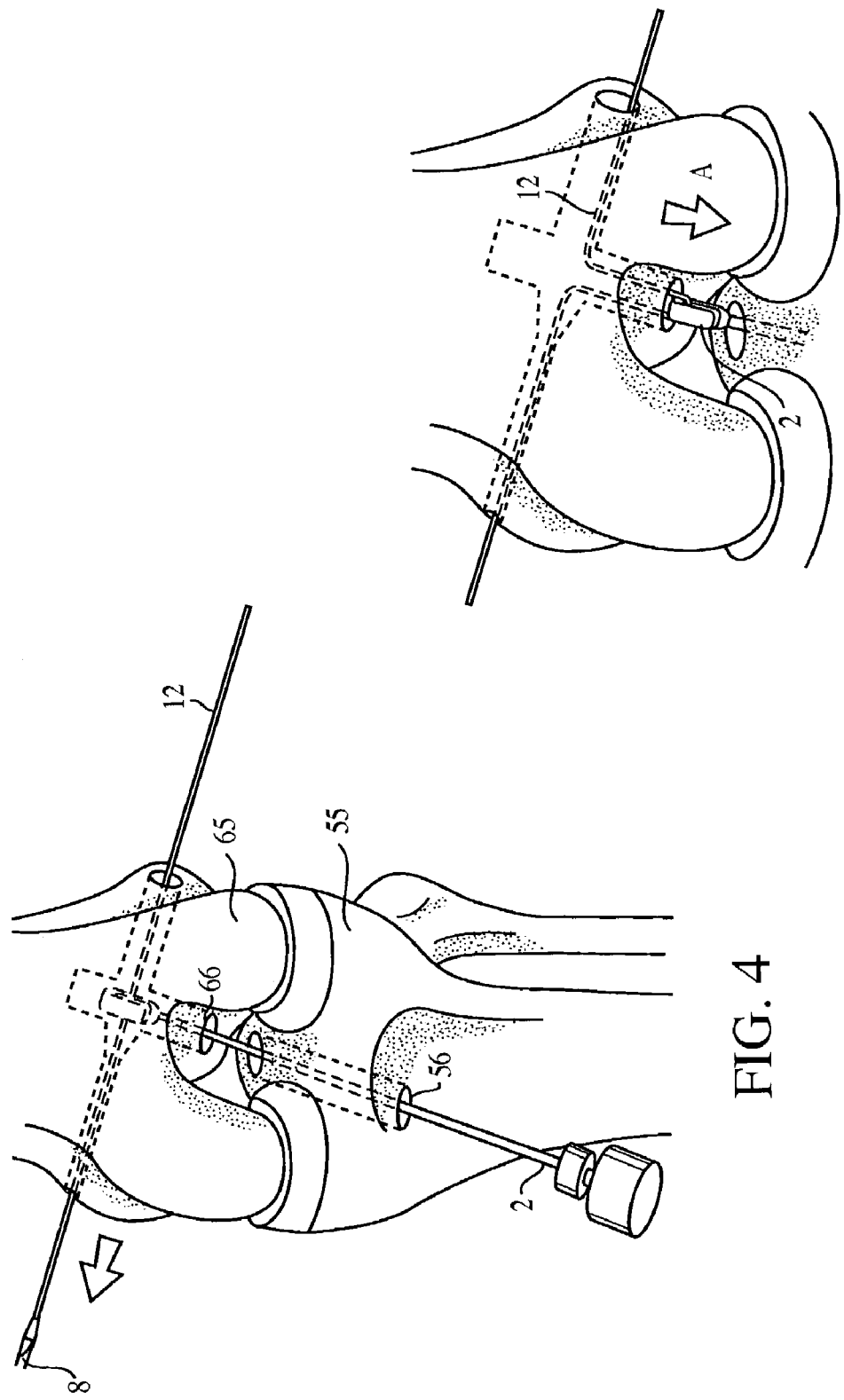

TRANSVERSE FIXATION TECHNIQUE FOR ACL RECONSTRUCTION USING BONE-TENDON-BONE GRAFT WITH LOOP AT END

This is a continuation-in-part of application Ser. No. 10/280,028, filed Oct. 25, 2002, which is a continuation-in-part of application Ser. No. 10/121,610, filed Apr. 15, 2002, now U.S. Pat. No. 6,537,319, which is a continuation of application Ser. No. 09/663,798, filed Sep. 18, 2000, now U.S. Pat. No. 6,371,124, which is a continuation of application Ser. No. 09/346,709, filed Jul. 2, 1999, now U.S. Pat. No. 6,132,433, which is a continuation of application Ser. No. 09/015,618, filed Jan. 29, 1998, now U.S. Pat. No. 5,918,604, which claims the benefit of U.S. Provisional Application Ser. No. 60/037,610, filed Feb. 12, 1997. This application also claims the benefit of U.S. Provisional Application Ser. No. 60/330,575, filed Oct. 25, 2001.

FIELD OF THE INVENTION

The present invention relates to surgical cross pin fixation of bone-tendon-bone (BTB) autografts and, more specifically, to reconstruction of the anterior cruciate ligament (ACL) using BTB graft fixation.

BACKGROUND OF THE INVENTION

Methods of ACL reconstruction using interference screw fixation are described in U.S. Pat. Nos. 5,211,647 and 5,320,626, the entire disclosures of which are incorporated herein by reference. In general, these methods of ACL reconstruction involve drilling a tunnel through the tibia, drilling a closed tunnel (socket) into the femur, inserting a substitute ACL graft into the tunnels, and securing the grafts to the walls of the tibial and femoral tunnels using interference screws.

Although interference screw attachment generally is secure, it is sometimes neither possible nor desirable to provide such fixation, particularly in the femoral tunnel. In revision situations, for example, where a previous reconstruction has been performed, placing a second femoral tunnel close to the previous tunnel may not be indicated.

A fixation technique that provides strong attachment of a graft in the femoral tunnel using a transverse implant is disclosed in U.S. Pat. No. 5,601,562, of common assignment with the present application, and incorporated by reference herein. The transverse implant is inserted through a loop in a tendon graft. A threaded portion of the implant screws into the bone as the implant is advanced with rotation into the repair site. The technique is disadvantageous, however, because the graft can become wrapped around the implant as it is rotated. In addition, this technique requires a forked insertion tool to lift the tendon graft into the femoral socket, and large tibial and femoral tunnels are needed to accommodate the forked insertion tool. As a result of the large tunnels, the graft can slide laterally and "wipe" back and forth along the fixation implant.

An improved method for loading tendons into a femoral socket is disclosed in U.S. Pat. No. 5,918,604, the entire disclosure of which is incorporated by reference herein. In this technique, a strand of suture or nitenol wire is drawn transversely across the femoral socket, and a loop of the strand is pulled down from the socket and out of the tibial tunnel. The tendon graft is passed through the loop, and the strand loop with tendon attached is lifted back into the femoral socket. A transverse implant is then advanced under the tendon graft, preferably by impact insertion to avoid wrapping of the tendon graft during insertion.

Although the technique disclosed in U.S. Pat. No. 5,918,604 is much improved over prior techniques and has come into widespread use, it does not provide for the use of a closed loop graft, such as a bone-tendon-bone graft or construct. Accordingly, there is a need for an improved fixation technique, particularly in cruciate ligament reconstructions, utilizing a bone-tendon-bone (BTB) graft, or construct.

SUMMARY OF THE INVENTION

The present invention overcomes the disadvantages of the prior art, such as those noted above, by providing a surgical method for loading BTB grafts into a joint and fixating the grafts using a transverse, intraosseous implant passing through a loop extending from the bone block. The inventive technique advantageously uses narrow tibial and femoral tunnels, like the technique of U.S. Pat. No. 5,918,604, and can be similarly implemented using a transverse implant that is advanced by impaction across the femoral socket.

As applied to the knee, the method includes the use of standard techniques to drill a longitudinal tunnel in the upper tibia. Subsequently, a femoral tunnel (socket) is formed, preferably in the lateral femoral condyle. Advantageously, the diameters of the tibial and femoral tunnels are made just large enough to accommodate a BTB graft in a snug fit. A tunnel hook provided with a capture slot and mounted on a cross-pin drill guide is inserted through the tibial tunnel and into the femur. A drill pin directed by the drill guide is installed transversely through the femur to intersect the femoral tunnel. The drill pin passes through the capture slot of the tunnel hook. A transverse channel is formed in the femur, preferably using a cannulated drill placed over the drill pin, to accommodate a threaded section of the transtibial implant.

A flexible graft passing strand, preferably a high strength suture, is attached to the drill pin and pulled through the femur, such that it passes through and is captured in the slot of the tunnel hook. The tunnel hook is then retracted completely from the femoral tunnel and out of the tibial tunnel, such that a loop of the flexible graft passing strand protrudes from the entrance to the tibial tunnel.

The loop of the flexible graft passing strand is captured by another loop of high-strength flexible strand material that is attached to one of the bone blocks of a bone-tendon-bone graft. The loop of the flexible graft passing strand is retracted into the femoral tunnel by pulling evenly on the medial and lateral ends of the graft passing strand. Optionally, the graft passing strand may be lifted into place by a beath pin connected to the strand attached to the bone block, the beath pin passing longitudinally through the femoral tunnel to exit the anterior lateral thigh.

As a result of either method, the BTB graft is drawn into the tibial tunnel. The graft passing strand can be replaced with a length of guide wire by attaching the wire to the graft passing strand and pulling the wire transversely across the femoral socket. A cannulated implant is placed over the wire and driven into the femur, preferably by impaction. The cannulated implant passes through the loop attached to the BTB graft, thus securing the graft in the femoral tunnel.

Other features and advantages of the present invention will become apparent from the following description of the invention which refers to the accompanying drawings.

BRIEF DESCRIPTION OF THE DRAWINGS

FIG. 4 illustrates a strand attached to a drill pin and being pulled through the femur according to the present invention.

FIG. 5 illustrates a loop of the strand being pulled by the hook and out through the femoral tunnel (socket) according to the present invention.

DETAILED DESCRIPTION OF THE PREFERRED EMBODIMENTS

Figure 1:
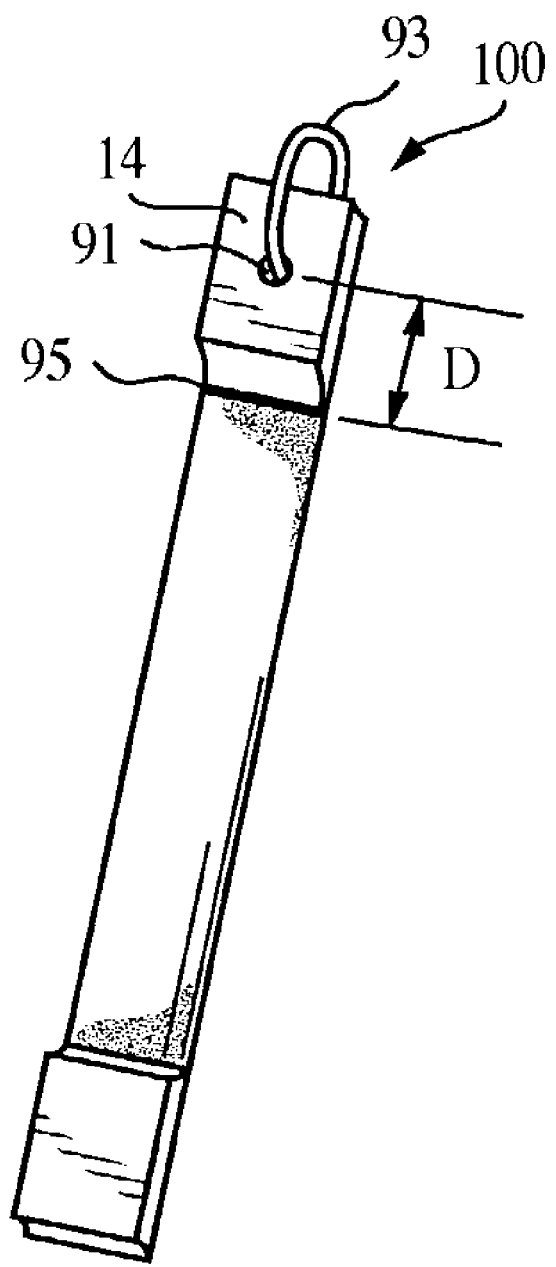
FIG. 1 is a schematic view of a BTB graft employed in a method according to the present invention.

Referring now to the drawings, where like elements are illustrated by like reference numerals, FIGS. 1–8 illustrate a transosseous fixation technique for a bone-tendon-bone (BTB) graft according to the present invention.

Referring to FIG. 1 and as applied to the knee, a bone-tendon-bone (BTB) graft 100 is harvested and measured as to length and diameter. A minimum diameter of 10 millimeters and a minimum length of 30 millimeters are preferred. The BTB graft 100 is fashioned so that a hole 91 is provided on femoral bone block 14.

Figure 2:
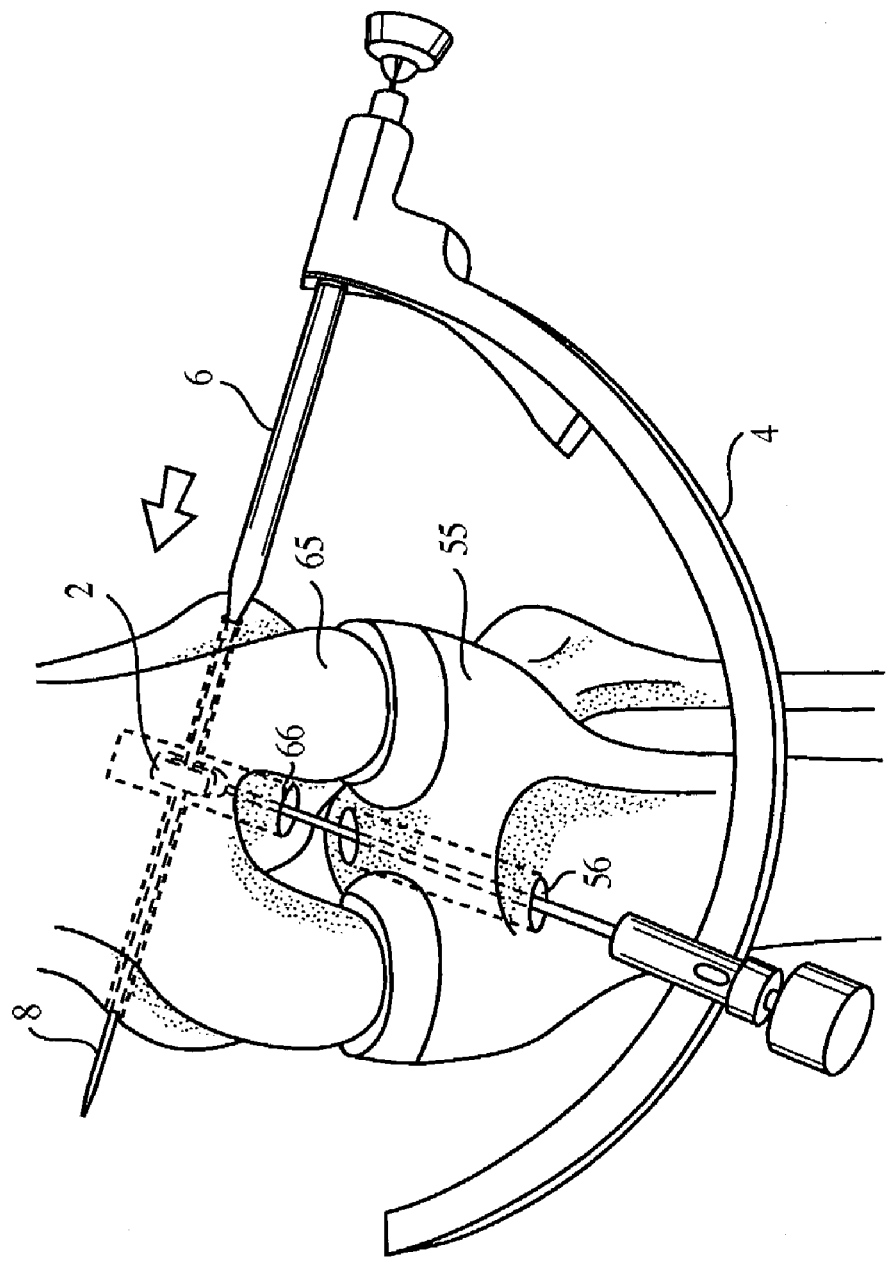
FIG. 2 is a schematic view of a hook and a drill pin mounted on a drill guide and disposed within the femoral tunnel (socket) according to the present invention.

Referring now to FIG. 2, the method of the present invention includes the use of standard techniques to drill a longitudinal tunnel 56 in tibia 55 and a femoral tunnel (socket) 66 in femur 65. The femoral tunnel 66 is over-drilled by a minimum of 5 millimeters.

A tunnel marking hook 2 (FIG. 2) is placed into the femoral tunnel 66 through the tibial tunnel 56. A mark on the hook indicating appropriate alignment is brought flush with the joint opening of the femoral tunnel 66. The marking hook 2 is secured to a C-ring cross-pin drill guide 4 such as those disclosed in U.S. Pat. Nos. 5,350,383 and 5,918,604, the disclosures of which are incorporated by reference herein. In this manner, a drill pin guide sleeve 6 on the drill guide 4 is secured to the lateral thigh in routine fashion. A 3-millimeter guide pin 8 drilled from lateral to medial passes through a capture slot formed in the tunnel marking hook 2.

Figure 3:
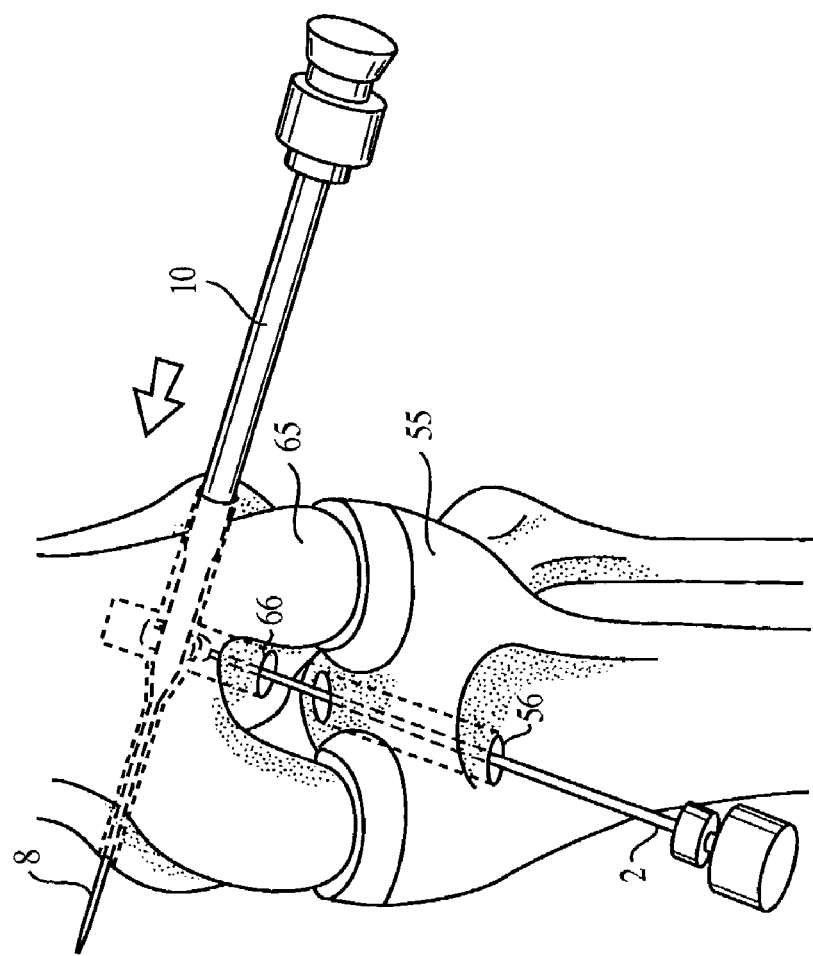
FIG. 3 is a schematic view of a step of forming a femoral channel for the transverse implant according to the present invention.
Figure 7:
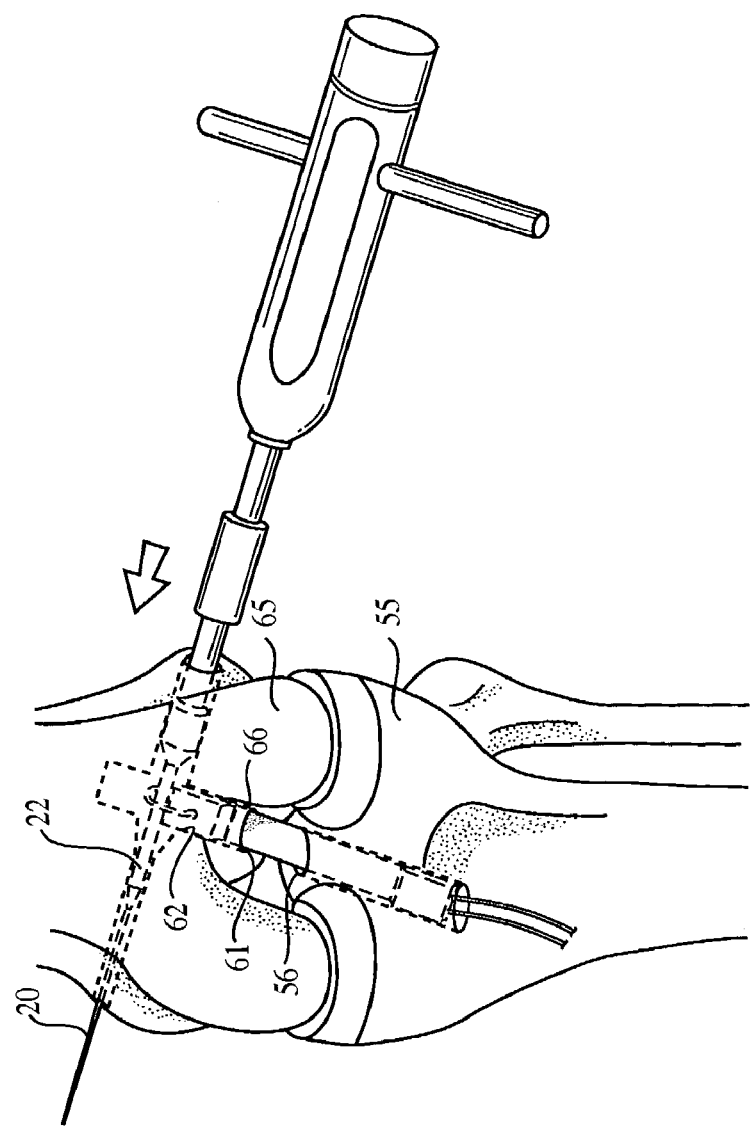
FIG. 7 illustrates the BTB graft, having been loaded through the longitudinal tibial tunnel and into the femoral tunnel (socket), being fixated using a transverse implant according to the present invention.
Figure 8:
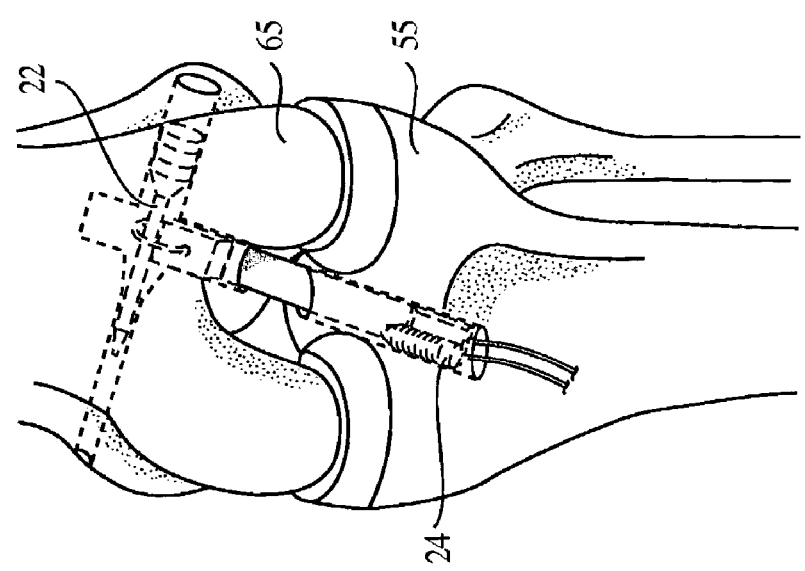
FIG. 8 illustrates a completed BTB graft repair including tibial fixation with an interference screw.

Referring now to FIG. 3, a 5 millimeter broach 10 is passed over the drill pin 8 and drilled through the medial cortex to create a pilot hole for the head of a transtibial implant 22 (FIGS. 7–8). In this manner, a channel is formed in the lateral femoral cortex to accommodate the remainder of the implant. The walls of the channel can be compacted, preferably using a dilator placed over the guide pin.

Next, and as illustrated in FIG. 4, a first flexible graft passing strand 12 is attached to the guide pin 8 and passed through the femur 65. Graft passing strand 12 preferably is either a strand of high strength suture sold by the present assignee under the tradename FiberWire, or a strand of nitinol wire. As shown in FIG. 5, withdrawing the marking hook 2 from the femoral and tibial tunnels 66 and 56, respectively, in the direction of arrow A pulls a loop 88 of the graft passing strand 12, captured in the capture slot 8 of the marking hook 2, out of the tibial tunnel 56.

Figure 6:
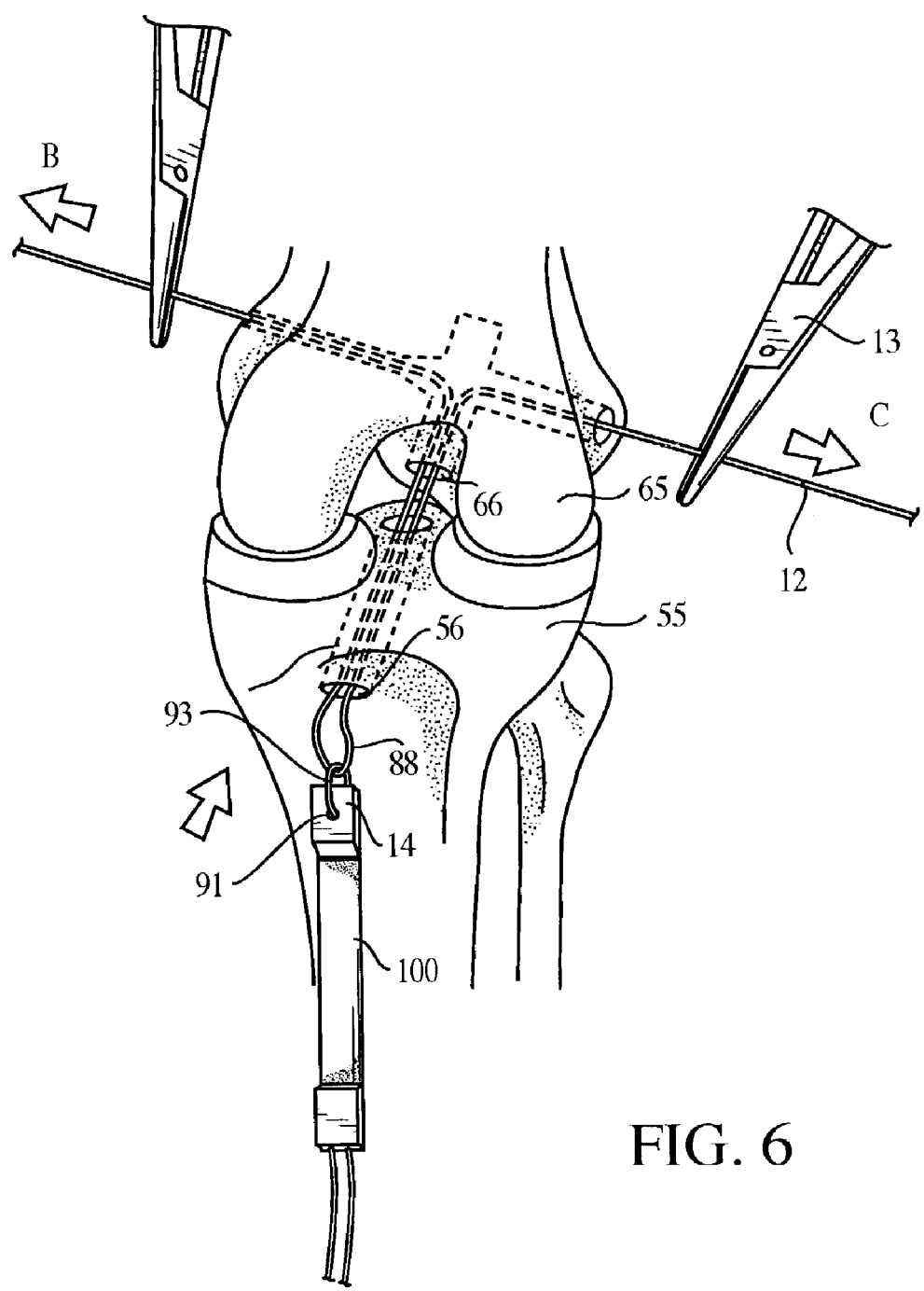
FIG. 6 illustrates the strand loop having been diverted through the tibial tunnel, capturing a ligament graft, and pulling the graft into the tibial tunnel according to the present invention.

Referring to FIG. 6, the graft passing strand 12, having been drawn outside the tibial tunnel 56, is connected to the femoral bone block 14 of BTB graft 100 by an attachment loop 93 formed through hole 91 in bone block 14 and around the loop of the graft passing strand 12. A preferred method of forming the loop is described below in connection with FIGS. 9–19.

Once the BTB graft 100 is connected to the graft passing strand 12, the BTB graft 100 is drawn into the tibial tunnel 56. This can be achieved by drawing on the ends of the graft passing strand 12 located on the medial and lateral sides of the femur in the direction of arrows B and C, as illustrated in FIG. 6. In lieu of or in addition to this technique, the BTB graft 100 may be drawn into the tibial tunnel 56 using a beath pin (not shown), connected to loop 93. The beath pin is passed inferiorly through the femoral tunnel 66 to exit the anterior lateral thigh to engage the loop of suture 93 and draw the graft into the tibial tunnel.

After bone block 14 of the BTB graft 100 is delivered into the femoral tunnel 66, proper positioning of the BTB graft 100 is checked by confirming that the bone-tendon junction 95 (FIG. 1) of the BTB graft 100 is flush to opening 61 of the femoral tunnel 66, the cancellous portion of the bone block 14 is flush with lateral wall 62 of the femoral tunnel 66, and the tendon is flush with the medial side of the tunnel 66.

The flexible strand 12 is then attached a length of nitinol guide wire 20 (FIG. 7). The nitinol wire is delivered laterally through the loop 93 provided on graft 100 and the femoral tunnel 66 by pulling the medial side of flexible suture strand 12, such that the wire 20 passes through both the medial and lateral sides of the femur. A guide wire introducer (Arthrex Part No. AR-4069) can be inserted over the lateral nitinol guide wire 20 to insure proper alignment of the BTB graft 100 and guide wire.

Referring to FIG. 8, femoral fixation is provided by a transosseous cannulated implant 22. The transosseous cannulated implant 22 is fed onto the guide wire 20 followed by an impactor. The implant 22 is gently impacted into position. Implant position and femoral fixation are confirmed prior to removing the guide wire 20.

Tibial fixation of the BTB graft 100 may be performed by various known methods, including interference screw fixation 24, which provides the most secure post-operative result; distal fixation with a cancellous screw using a post and washer technique; and a belt buckle staple technique utilizing a pair of ligament staples.

Various endoscopic techniques and instruments relating to graft fixation are known in the prior art and can be used in the practice of the present invention. U.S. Pat. No. 5,320,636 to Schmieding discusses an endoscopic drill guide for graft tunnel location. U.S. Pat. No. Des. 378,780 illustrates a cannulated headed reamer, which can be used in femoral socket formation. Similarly, U.S. Pat. Nos. 5,269,786 and 5,350,383 disclose drill guides for location of bone tunnels.

Figure 9:
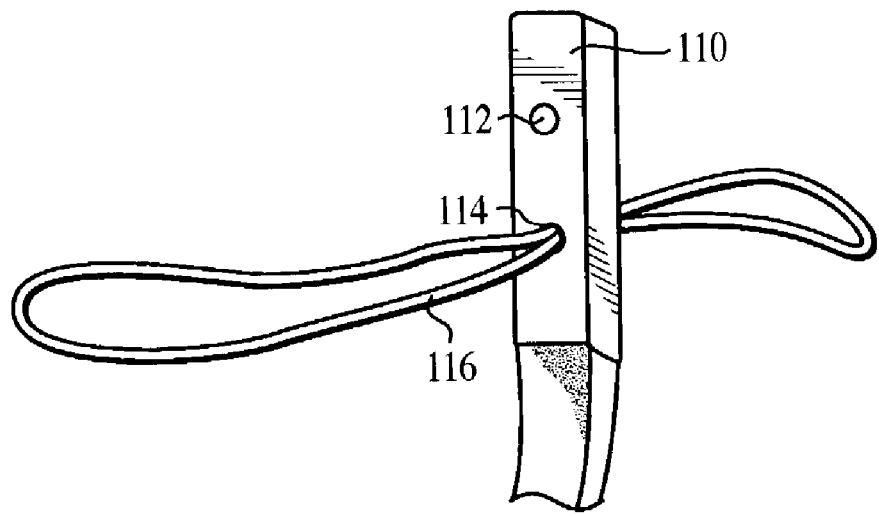
FIGS. 9–19 illustrate steps in a preferred method of forming a loop on a bone block portion of a bone-tendon-bone graft according to the present invention.
Figure 10:
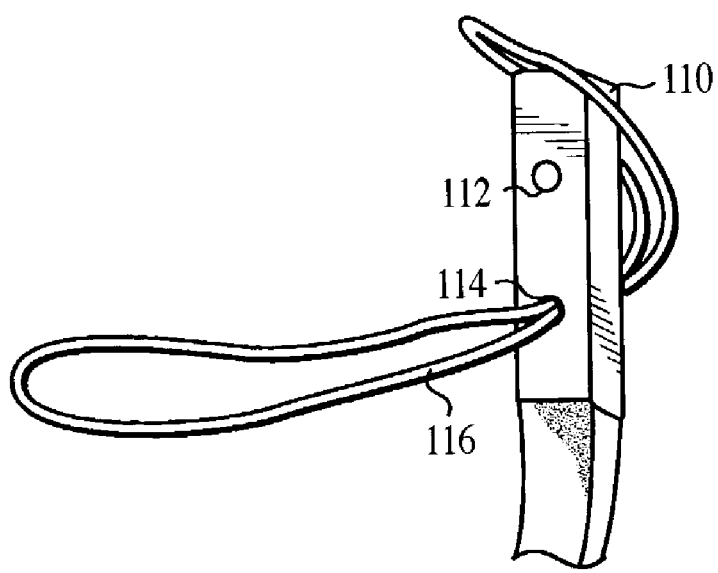
Figure 11:
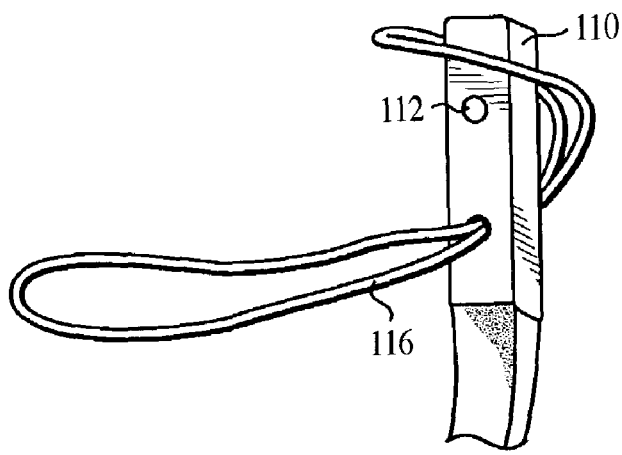
Figure 12:
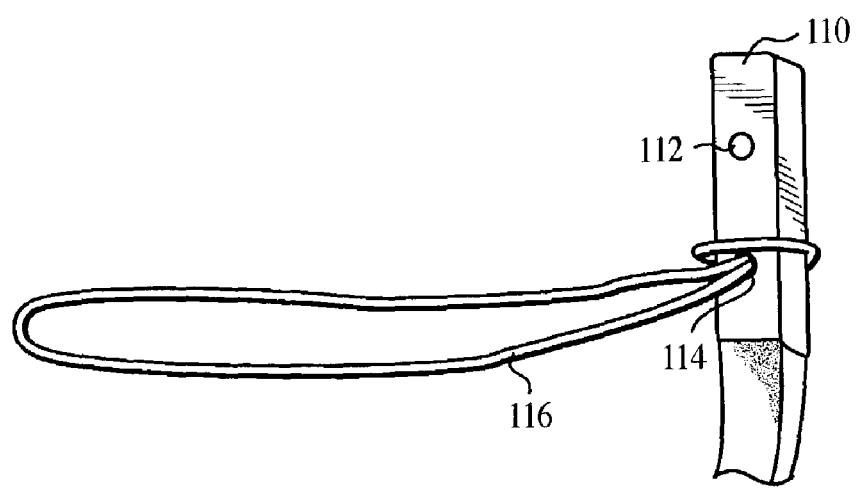
Figure 13:
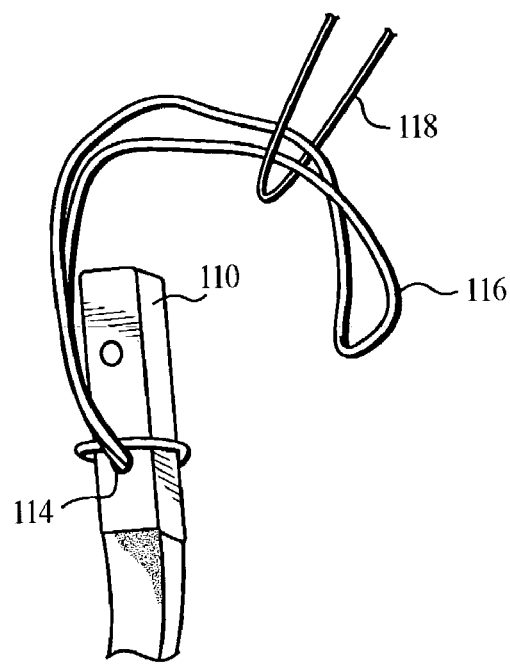
Figure 14:
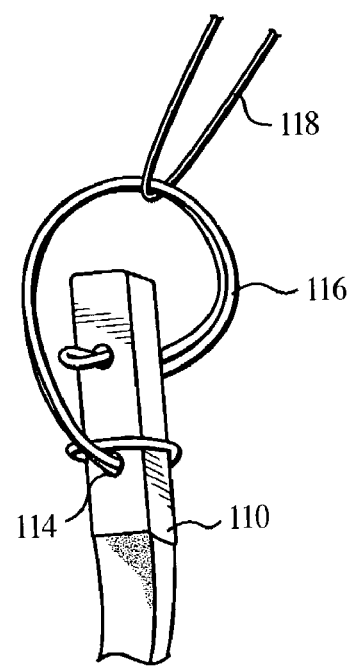
Figure 15:
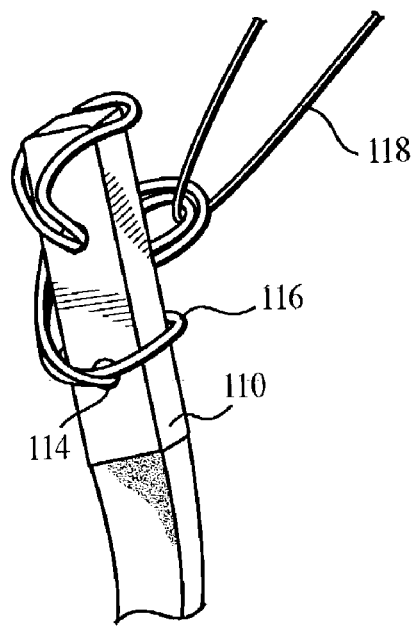
Figure 16:
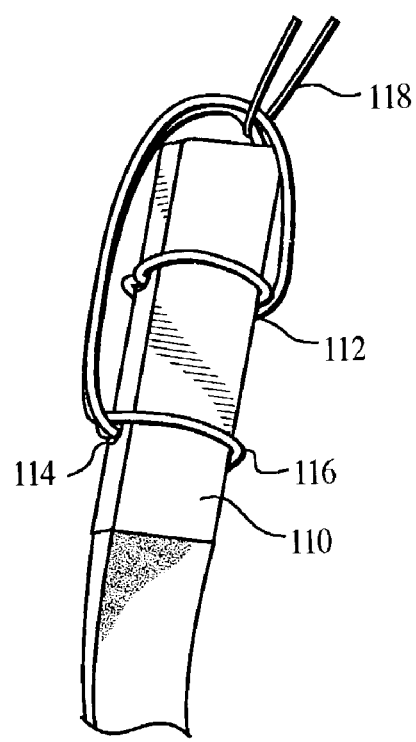
Figure 17:
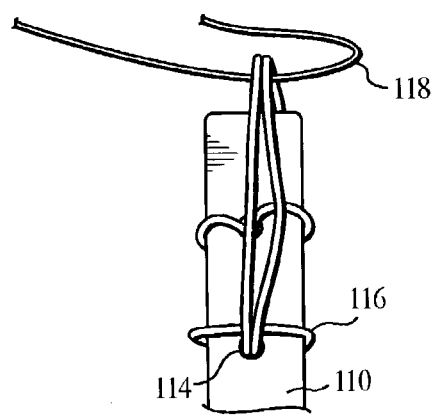
Figure 18:
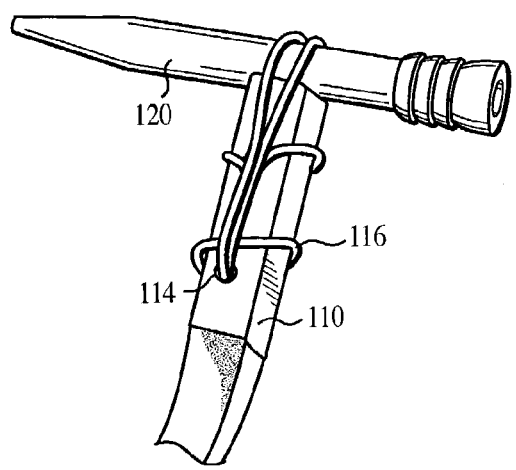
Figure 19:
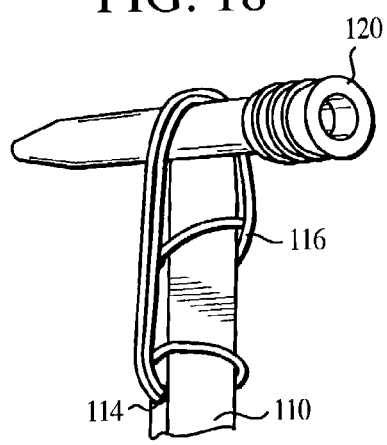

A preferred method of forming loop 93 on a bone block is illustrated in FIGS. 9–19. Referring initially to FIG. 9, a block 110, representative of a bone block portion of a bone-tendon-bone graft, is provided with two transverse openings 112 and 114. A looped length of suture material 116 is passed through the lower opening 114. As shown in FIGS. 10–12, one end of loop 116 is brought over the upper end of block 110, and tightened around the block 110. Referring to FIGS. 13 and 14, the remaining free end of suture loop 116 is brought upwardly through a wire loop 118 and over the top of block 110 to be passed back through the upper opening 112. As shown in FIG. 15, the end of loop 116 is passed over the top of the block 110 and is tightened around the block 110. The wire loop 118 is used to draw a section of loop 116 into position over the top of block 110 to form a loop for secure attachment of the graft, as shown in FIG. 16. FIG. 17 illustrates the completed loop construct with the wire loop 118 remaining in place. The loop is used to draw the bone block and tendon into the tibial tunnel. FIGS. 18 and 19 illustrate the placement of a securing pin 120, as would be used in the surgical knee reconstruction to stabilize and secure the knee construct.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of anterior cruciate ligament reconstruction, comprising the steps of:
   forming a tibial tunnel between an anterior tibial surface and the tibial plateau;
   forming a femoral tunnel having an opening and a sidewall; introducing a strand into the femoral tunnel through said sidewall;
   pulling said strand through said opening of said femoral tunnel and down through said tibial tunnel;
   attaching said strand to a loop extending from a bone block of a bone-tendon-bone graft; and
   pulling said strand attached to said bone block of said bone-tendon-bone graft into said femoral tunnel.

2. The method of claim 1, further comprising the step of supporting said bone-tendon-bone graft in said femoral tunnel.

3. The method of claim 2, wherein said step of supporting said bone-tendon-bone graft in said femoral tunnel is conducted using a transosseous implant passed through the loop formed on the bone block.

4. The method of claim 1, further comprising the step of forming the loop around said strand after said step of pulling said strand through said opening of said femoral tunnel and down through said tibial tunnel.

5. The method of claim 1, wherein said step of pulling said strand through said opening of said femoral tunnel and down through said tibial tunnel is performed by engaging said strand with a hook.

6. The method of claim 5, further comprising the step of inserting said hook into said femoral tunnel and retracting said hook and said strand engaged thereto from said femoral tunnel.

7. A method of anterior cruciate ligament reconstruction, the method comprising the steps of:
   forming a tibial tunnel between an anterior tibial surface and the tibial plateau; forming a femoral tunnel having an opening and a sidewall; introducing a suture into the femoral tunnel through said sidewall;
   pulling said suture through said opening of said femoral tunnel and down through said tibial tunnel;
   attaching said suture to a loop extending from a bone block of a bone-tendon-bone graft; lifting said bone block of said bone-tendon-bone graft into said femoral tunnel; and
   supporting said bone-tendon-bone graft into said femoral tunnel by using a transosseous implant.

8. The method of claim 7, further comprising the step of introducing a nitinol wire through said hole of said bone block of said bone-tendon-bone graft after the bone block of the bone-tendon-bone graft has been lifted into the femoral tunnel, and advancing a cannulated implant along the wire and through the loop formed on bone block to support the graft in the femoral tunnel.

* * * * *